(12) United States Patent
Yu

(10) Patent No.: US 10,832,422 B2
(45) Date of Patent: Nov. 10, 2020

(54) ALIGNMENT SYSTEM FOR LIVER SURGERY

(71) Applicant: Sony Corporation, Tokyp (JP)

(72) Inventor: Liangyin Yu, Fremont, CA (US)

(73) Assignee: SONY CORPORATION, Tokyo (JP)

( * ) Notice: Subject to any disclaimer, the term of this patent is extended or adjusted under 35 U.S.C. 154(b) by 333 days.

(21) Appl. No.: 16/025,949

(22) Filed: Jul. 2, 2018

(65) Prior Publication Data
US 2020/0005473 A1 Jan. 2, 2020

(51) Int. Cl.
*G06T 7/33* (2017.01)
*G06T 7/73* (2017.01)
(Continued)

(52) U.S. Cl.
CPC ............ *G06T 7/337* (2017.01); *A61B 1/3132* (2013.01); *A61B 6/032* (2013.01); *A61B 6/5247* (2013.01); *G06T 3/0068* (2013.01); *G06T 7/0014* (2013.01); *G06T 7/74* (2017.01); *G06T 7/85* (2017.01); *G06T 11/003* (2013.01); *H04N 13/25* (2018.05); *G06T 2207/10081* (2013.01); *G06T 2207/20101* (2013.01)

(58) Field of Classification Search
CPC ..... A61B 1/3132; A61B 6/032; A61B 6/5247; G06T 11/003; G06T 2207/10068; G06T 2207/10081; G06T 2207/20101; G06T 2207/30056; G06T 3/0068; G06T 7/0014; G06T 7/33; G06T 7/337; G06T 7/579; G06T 7/593; G06T 7/74; G06T 7/75; G06T 7/85; H04N 13/25
See application file for complete search history.

(56) References Cited

U.S. PATENT DOCUMENTS

2005/0049478 A1   3/2005 Kuduvalli
2017/0084036 A1*  3/2017 Pheiffer ................... G06T 7/35
(Continued)

OTHER PUBLICATIONS

C.T. Metz et al; "GPU accelerated alignment of 3-D CTA with 2-D X-ray data for improved guidance in coronary interventions" http://ieeexplore.ieee.org/document/5193213/ ; 2009 IEEE International Symposium on Biomedical Imaging: From Nano to Macro—Jul. 2009.
Plantefeve Rosalie et al: "Automatic Alignment of Pre and Intraoperative Data Using Anatomical Landmarks for Augmented Laparoscopic Liver Surgery", Oct. 16, 2014 (Oct. 16, 2014)' International Conference on Computer Analysis of Images and Patterns. CAIP 2017: Computer Analysis of Images and Patterns; [Lecture Notes in Computer SCI ENCE; LECT.Notes Computer], Springer, Berlin, Heidelberg.
(Continued)

*Primary Examiner* — Manuchehr Rahmjoo
(74) *Attorney, Agent, or Firm* — Trellis P Law Group, PC

(57) ABSTRACT

A method for automatic registration of landmarks in 3D and 2D images of an organ comprises: using a first set of coordinates of identified first, second and third landmarks of the organ, derived from a 3D surface representation of the organ, and a second set of coordinates of the landmarks, derived from 2D laparoscopic images of the organ, to register the three landmarks as identified in the 3D surface representation with the three landmarks as identified in the 2D images. The third landmark comprises a plurality of points defining a path between two points characterizing the first and second landmarks The identification of the first, second and third landmarks in the 3D representation and the 2D images, the derivation of the first and second sets of coordinates, and the registration, based on the derived first and second sets of coordinates, are performed automatically.

14 Claims, 5 Drawing Sheets

(51) Int. Cl.

| | | |
|---|---|---|
| G06T 7/80 | (2017.01) | |
| H04N 13/25 | (2018.01) | |
| A61B 1/313 | (2006.01) | |
| A61B 6/03 | (2006.01) | |
| A61B 6/00 | (2006.01) | |
| G06T 3/00 | (2006.01) | |
| G06T 7/00 | (2017.01) | |
| G06T 11/00 | (2006.01) | |

(56) References Cited

U.S. PATENT DOCUMENTS

2017/0178349 A1   6/2017   Ketcha
2018/0158201 A1   6/2018   Thompson

OTHER PUBLICATIONS

Ramalhinho Joao et al: "A pre-operative planning framework for global registration of laparoscopic ultrasound to CT images", International Journal of Computer Assisted Radiology and Surgery, Springer, DE, vol. 13, No. 8, Jun. 2, 2018 (Jun. 2, 2018).
Heiselman Jon S et al: "Characterization and correction of intraoperative soft tissue deformation in image-guided laparoscopic liver surgery", Journal of Medical Imaging, Society of Photo-Optical Instrumentation Engineers, 1000 20th St. Bellingham WA 98225-6705 USA, vol. 5, No. 2, Apr. 2018 (Apr. 2018).

* cited by examiner

ALIGNMENT SYSTEM FOR LIVER SURGERY

BACKGROUND

Laparoscopic surgery is a minimally invasive type of abdominal surgery, involving the use of an optical imaging system—a laparoscope—sending real-time images to a video monitor during the surgical procedure. It is necessary to carry out CT imaging before surgery, in preparation for proper surgical execution, and then make use of the results in relation to the 2-D laparoscopic video imaging obtained when the patient is actually on the surgical table.

In current practice, the task of aligning the 2-D images obtained in real-time during surgery to the previously generated CT images, typically reconstructed to create a 3-D representation of the organ of interest, is performed either manually or semi-automatically. In both cases, this means relying on the skills of an individual or team during surgery, requiring them to perform a difficult and challenging image processing task in addition to the surgery itself. The image alignment problem is made even harder if organ deformation occurs during surgery, as it often does.

There is, therefore, a need to provide a fully automatic method of carrying out alignment between CT 3-D images, obtained pre-operatively, and 2-D video images, obtained during surgery. Liver surgery is just one application in which such an automatic image alignment method would be of great value.

SUMMARY

Embodiments of the present invention generally relate to methods and systems that provide automatic registration of landmarks in 3D and 2D images of an organ. In one embodiment, a method comprises using a first set of coordinates of identified first, second and third landmarks of the organ, derived from a 3D surface representation of the organ, and a second set of coordinates of the identified first, second and third landmarks of the organ, derived from 2D laparoscopic images of the organ, to register the landmarks as identified in the 3D surface geometry with the landmarks as identified in the 2D images. The identification of the first, second and third landmarks in the 3D and 2D images is performed automatically; the derivation of the first and second sets of coordinates is performed automatically; and the registration, based on the derived first and second sets of coordinates, is performed automatically.

In another embodiment, an apparatus comprises one or more processors; and logic encoded in one or more non-transitory media for execution by the one or more processors. When executed, the logic operates to automatically register landmarks in 3D and 2D images of an organ, wherein the automatic registration comprises using a first set of coordinates of identified first, second and third landmarks of the organ, derived from a 3D surface representation of the organ, and a second set of coordinates of the identified first, second and third landmarks of the organ, derived from first and second 2D laparoscopic images of the organ, to register the landmarks as identified in the 3D surface image with the landmarks as identified in the 2D images. The identification of the first, second and third landmarks in the 3D and 2D images is performed automatically; the derivation of the first and second sets of coordinates is performed automatically; and the registration, based on the derived first and second sets of coordinates, is performed automatically.

A further understanding of the nature and the advantages of particular embodiments disclosed herein may be realized by reference to the remaining portions of the specification and the attached drawings.

DETAILED DESCRIPTION OF EMBODIMENTS

Embodiments described herein provide a surgeon or surgical team, during a laparoscopic procedure, with a 2D representation of 3D landmarks of the organ or region of interest aligned to the current 2D laparoscopic viewpoint to a usefully high degree of accuracy. It is assumed that 3-D representations of that organ or region were obtained and made available for study pre-operatively, and that 2-D laparoscopic images of that organ or region are being obtained in real time during surgery.

The present invention offers benefits over current approaches to alignment, which are time-consuming and demand specialized skills. Instead of requiring significant input from a human operator at various stages of the image alignment process, new methods of carrying out these stages have been developed, these methods being particularly suited to implementation by a computer-based processing system, operating automatically. Moreover, it does not depend, as current practice typically does, on the use of additional specialized equipment such as ultrasound imaging systems and tracking tools.

In the following discussion, the word "automatic" should be taken as meaning that the corresponding processing is carried out by software, without needing human intervention after the process is initiated.

Figure 1:
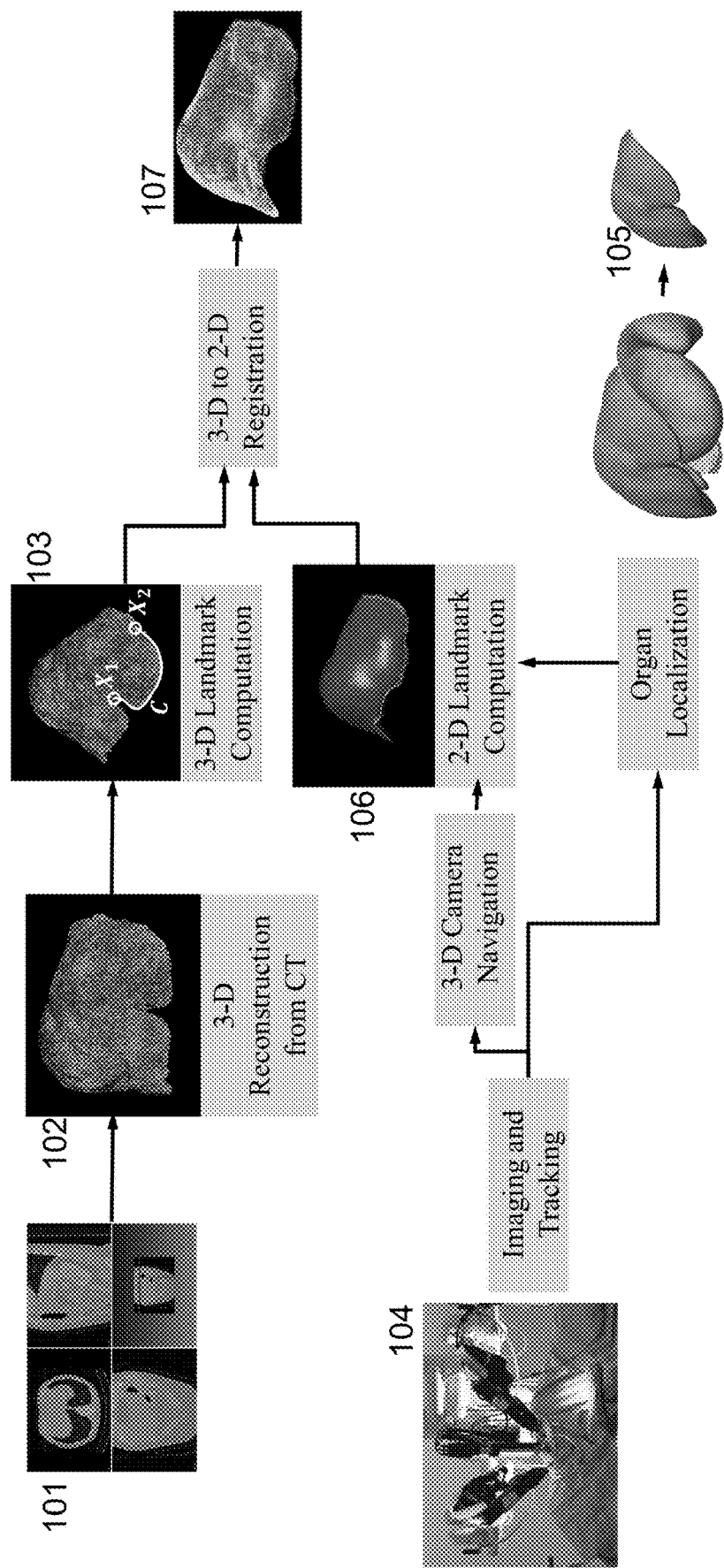
FIG. 1 is a schematic overview of an alignment method according to one embodiment of the present invention.

FIG. 1 illustrates an overview of an alignment method according to one embodiment of the present invention. Prior to surgery, a series of CT images 101 showing the organ of interest is generated, and a 3D surface reconstruction 102 is automatically created. At least three landmarks are identified on the surface reconstruction, the first and second, $X_1$ and $X_2$, being points, and the third being a plurality of points positioned along a readily distinguishable path C, which may for example be a ridge or furrow, between $X_1$ and $X_2$. A first set of coordinates for the three landmarks is automatically derived, and may be shown in an annotated 3D surface reconstruction 103. The coordinates for each landmark considered separately may be termed corresponding "subsets" of coordinates.

An imaging system 104, that includes a laparoscopic camera, and may optionally include one or more tracking sensors, is used during surgery to generate a series of at least three 2D images showing the organ of interest as well as, in general, surrounding material within the body. An organ localization process 105 may be carried out to aid in distinguishing the organ of interest in the images. This localization process will not be discussed further in this disclosure, as there are several well-known methods of achieving localization. On each of the 2D images, one or more of the same three landmarks $X_1$, $X_2$ and C are automatically identified. A second set of coordinates for the three landmarks is derived from the three 2D images. Again, the coordinates for each landmark considered separately may be termed corresponding "subsets' of coordinates.

Registration calculations are then carried out automatically on the first and second sets of coordinates, in a sense "reconciling" coordinates derived from the 3D and 2D images. The end result is a 2D representation 107 of the organ from the primary viewpoint (in terms of pose and orientation) of the laparoscopic camera, showing the 3D landmarks aligned to this viewpoint.

Figure 2:
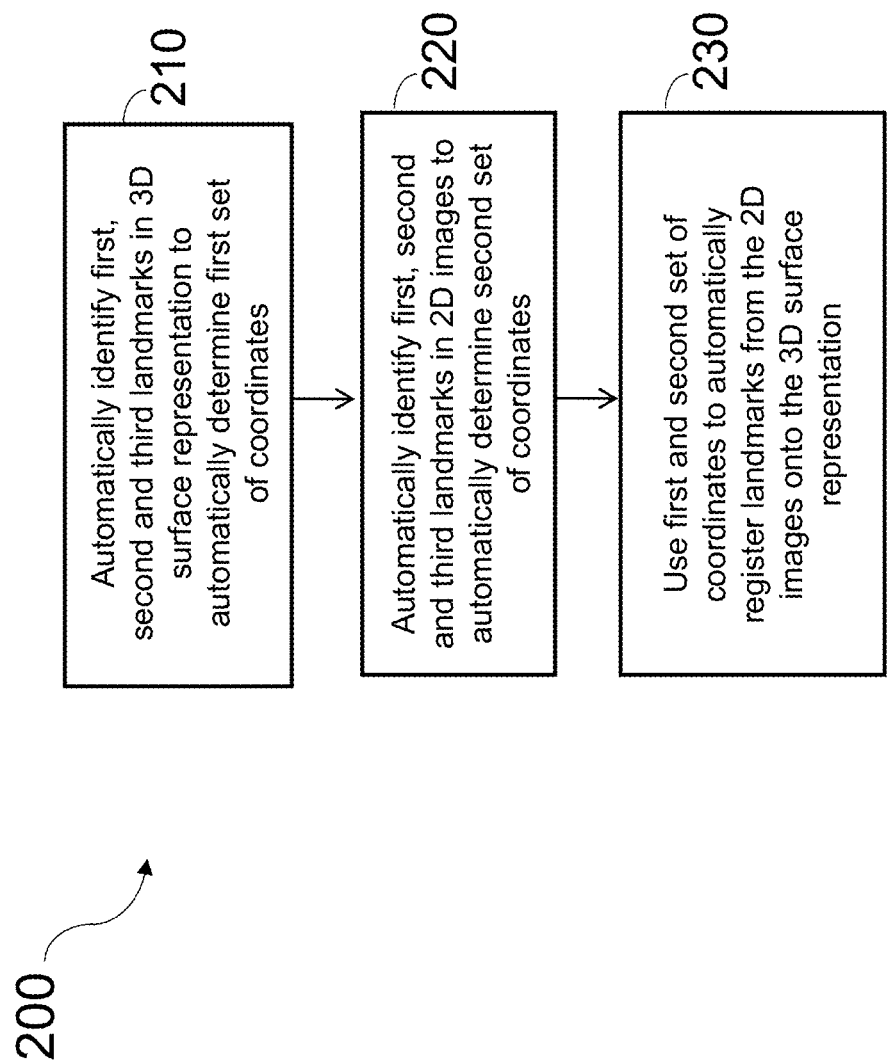
FIG. 2 is a flowchart of an alignment method according to one embodiment of the present invention.
Figure 4:
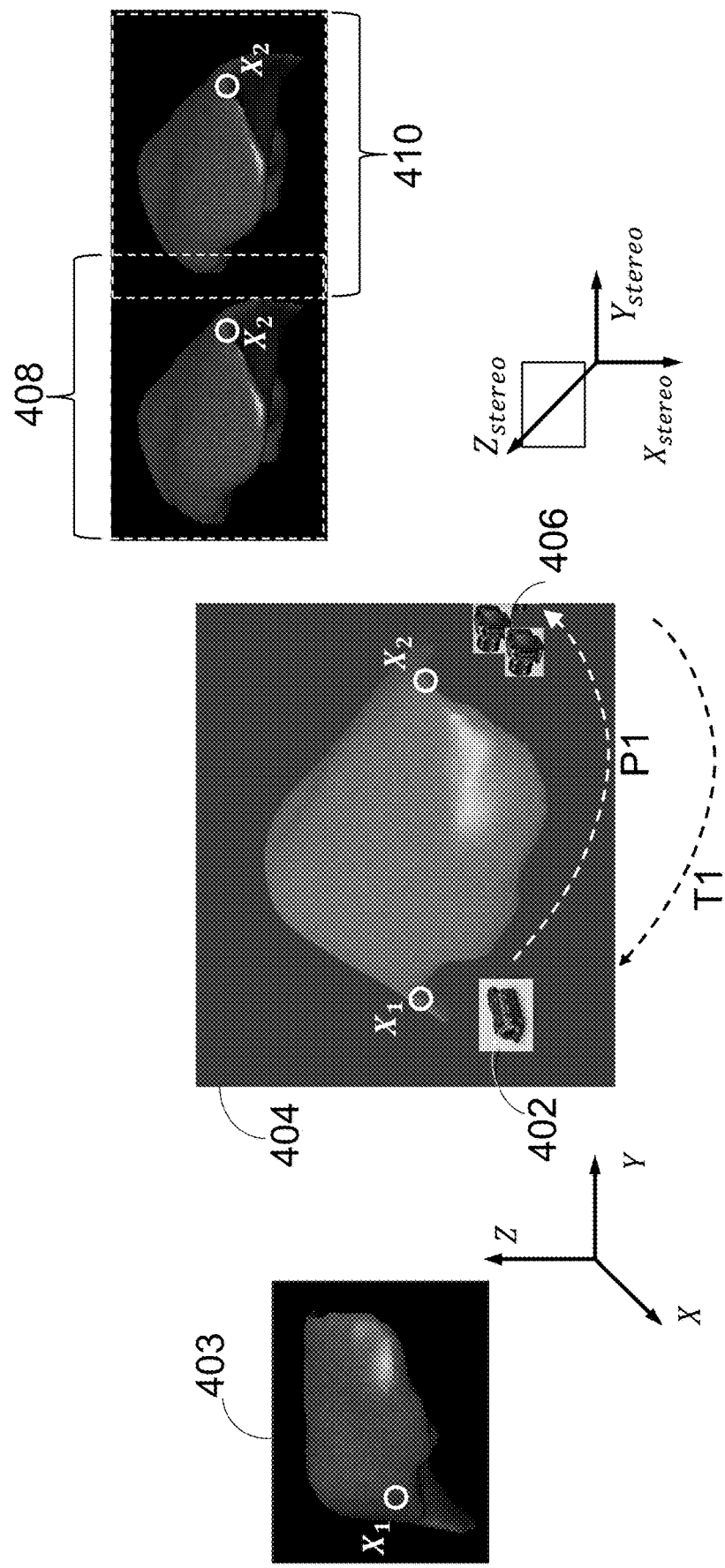
FIG. 4 schematically illustrates a method of transferring landmark coordinates between frames of reference used in one embodiment of the present invention.
Figure 5:
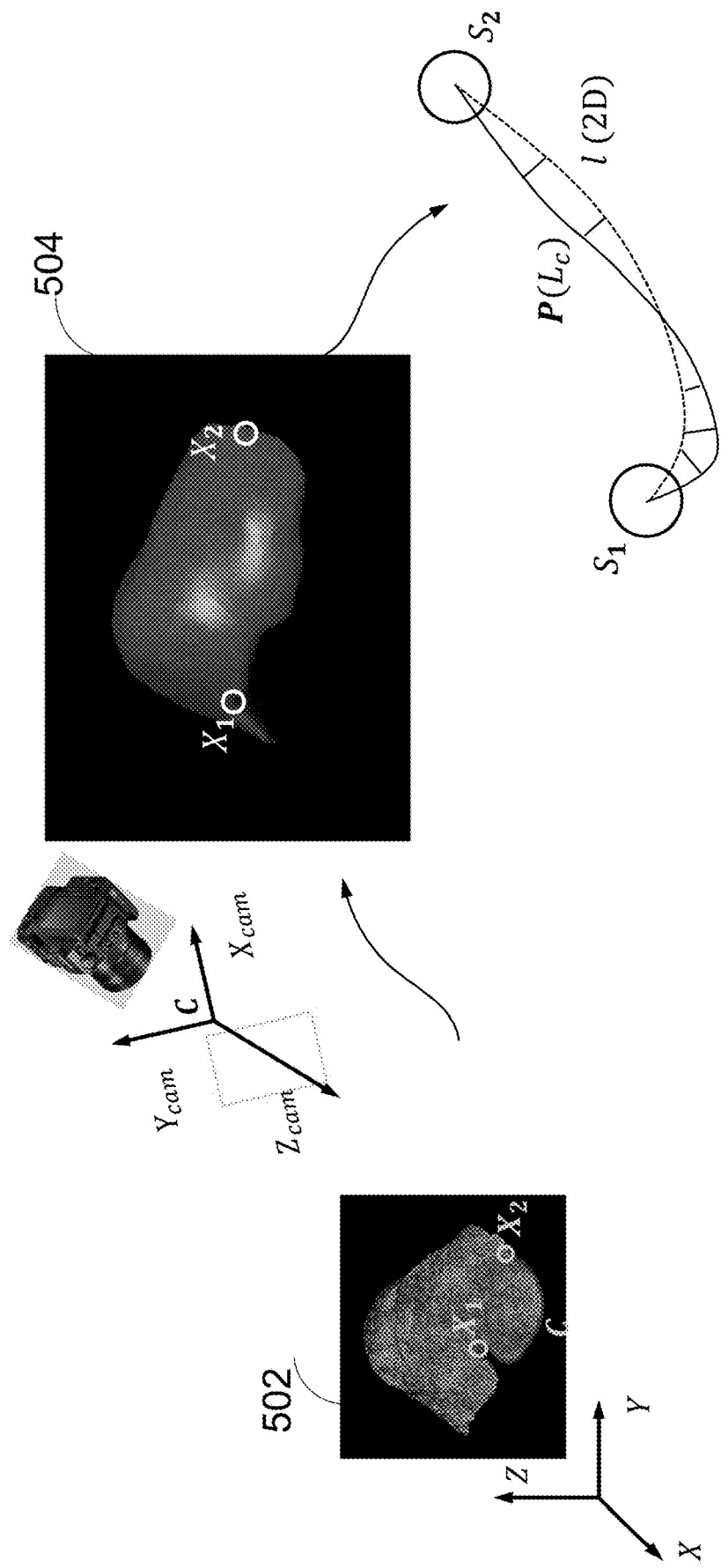
FIG. 5 schematically illustrates a method of registering landmark coordinates between a 3D representation and real-time 2D images in one embodiment of the present invention.

FIG. 2 is a high level flowchart of an alignment method 200 according to one embodiment of the present invention, showing relatively coarse steps 210, 220 and 230. At step 210, prior to surgery, first, second and third landmarks are automatically identified in a 3D surface representation, to automatically determine a first set of coordinates. At step 220, first, second and third landmarks are automatically identified in a series of at least three 2D images to automatically determine a second set of coordinates. Further details of step 220 are illustrated in FIG. 4 and the discussion thereof, presented below. At step 230, the first and second set of coordinates are used to automatically register the landmarks on the 3D surface representation in a way that corresponds to the pose and orientation at which a primary one of the three 2D images was captured. Further details of step 230 are illustrated in FIG. 5 and the discussion thereof, presented below.

Figure 3:
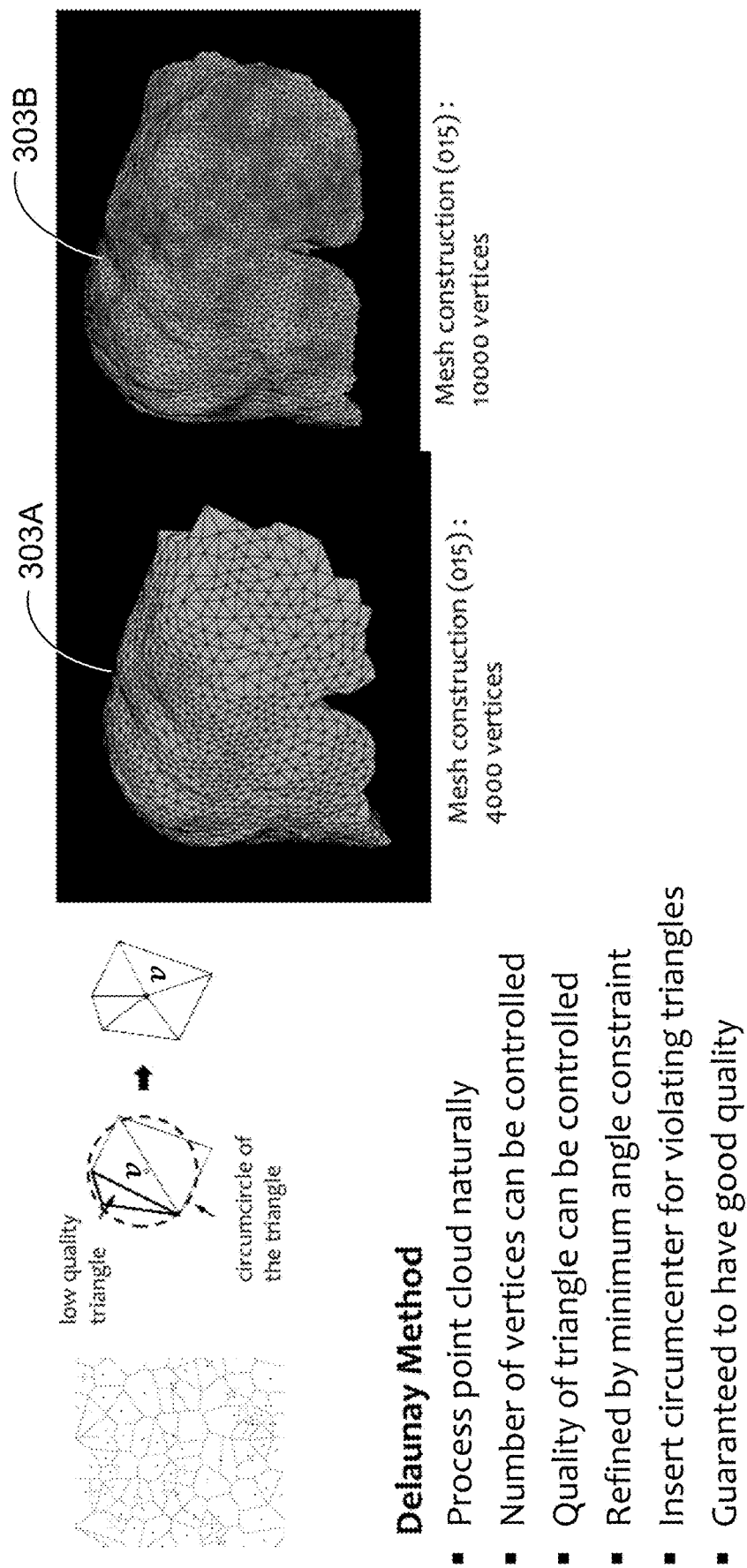
FIG. 3 schematically illustrates one type of 3D reconstruction used in one embodiment of the present invention.

The 3D surface representation used as an input to step 210 is generated with the use of a plurality of CT images, using well known image processing techniques. FIG. 3 schematically illustrates one type of 3D reconstruction used in one embodiment of the present invention. This is the Delaunay method, producing as an output a 3D surface representation such as 303A or 303B, corresponding to representation 102 in FIG. 2.

Landmarks (of at least two points and one path between them) are automatically identified on 3D surface representation 102 by computer vision and graphics methods that are well known in the art. A first set of coordinates for the landmarks may then be automatically generated.

During surgery, a laparoscopic camera positioned at a first location with a primary pose and orientation captures a primary 2D image of the organ or region of interest, showing at least one of the point landmarks, $X_1$ for example, seen in the embodiment illustrated in FIG. 4. In this embodiment first camera 402 captures primary 2D image 403, in which landmark $X_1$ (indicated by a white circle) is clearly visible near the left lower corner. Camera 402 is positioned at a first location relative to the organ of interest as shown in schematic representation 404 in the center of this figure. It should be noticed that landmark $X_2$ near the top right corner is typically partly obscured in image 403, hidden, for example, by intervening organ tissue. Part of landmark C may also be partly obscured in this way in image 403.

Landmark $X_1$ is identified using computer vision and computer graphics methods to identify the high curvature feature at the liver boundary, and its 2D coordinates are automatically generated in the frame of reference of camera 402, indicated by axes X, Y, Z.

First camera 402 is then moved along a path (indicated by dashed white line P1) to a second location, as close as practically possible to second camera 406, the motion of first camera 402 between the two locations being tracked in 3D, using sensing technology well known in the art, such as an optical or electromagnetic tool tracker.

Second camera 406, comprising in the illustrated embodiment a stereo camera, operates in a second frame of reference $X_{stereo}$, $Y_{stereo}$, $Z_{stereo}$, capturing two 2D images, shown as 408 and 410 in the composite image (formed from overlapping these images) at the top right of the figure. Second landmark $X_2$ is visible in each of these images 408, 410 although first landmark $X_1$ may be partly obscured. Landmark $X_2$ is identified using the same or similar methods to that used to identify $X_1$ and its coordinates in the $X_{stereo}$, $Y_{stereo}$, $Z_{stereo}$ frame of reference are automatically generated.

In the shown embodiment, because images 408, 410 are taken by a stereo camera, therefore from slightly laterally displaced positions, it is possible to determine positional information for landmark $X_2$ in terms of depth from the camera as well as in the plane of each image. Analysis of this information along with analysis of tracking data regarding camera 402 yields data, typically in the form of a transformation matrix, that allow transformation of the coordinates of $X_2$ from the $X_{stereo}$, $Y_{stereo}$, $Z_{stereo}$ frame of reference to the X, Y, Z frame of reference of camera 402 as it took the first 2D image. The transformation of coordinates of the second landmark is indicated by dashed line T1. The 2D coordinates of $X_2$ are then obtained by projecting the 3D coordinate information onto the image plane of camera 402 in the X, Y, Z frame of reference.

As discussed above, FIG. 4 schematically illustrates one embodiment of the present invention, showing a method of transferring or transforming landmark coordinates from one frame of reference to another, where a first camera captures a first image at a first location, the image showing a first landmark, and then moves to a second location, where a second, stereo camera captures a pair of stereo images each showing a second landmark.

In another embodiment, the second camera may not be a stereo camera as such, but a standard camera that is moved slightly between capturing second and third images in the vicinity of the second location, each image showing slightly different views of the second landmark, and therefore still allowing depth data to be generated.

In yet another embodiment of the present invention, the second camera takes not just a pair of images, but three or more images in the vicinity of the second location. Given that each of these three or more images is captured from a slightly different position in the vicinity of the second location, analysis of these images will again allow the generation of landmark coordinates in 3D, possibly at even higher accuracy than provided if only one pair of images were taken.

In other embodiments, instead of a second camera, the first camera is used to capture not only the primary first 2D image at the first location, but also the second and third (and optionally, more) 2D images in the vicinity of the second location.

It should be understood that the term "in the vicinity of" used throughout this disclosure means that the positions of the camera or cameras in question are made close enough that images captured from those positions overlap such that triangulation methods well known in the art can be applied to derive information on depth of features visible in those images.

FIG. 5 schematically illustrates a method of registering landmark coordinates between a 3D representation and real-time 2D images in one embodiment of the present invention. The positions of landmarks X1 and X2, previously established from the 3D representation 502, are projected onto the plane of real time laparoscopic 2D image 504 using an estimate of the position and orientation of the camera capturing 504 (the first 2D image in the terminology used above), the estimate being derived from an optimization process such as the one described below. A camera projection matrix is typically generated and used in carrying out this projection. Superimposed on image 504 are markers (shown as white rings) indicating the positions of X1, determined directly from image 504, and X2, determined by transformation of coordinates established from the second and third 2D images, as described above.

An explanatory illustration to the lower right of image 504 shows circular zones S1 and S2, indicating the projected positions of landmarks X1 and X2, as well as a projection $P(L_C)$ of the third landmark, the 3D pathway between the first two landmarks. Also shown is dashed line 1 (2D), derived from the 2D laparoscopic images, representing the third landmark. The error between the path projected from the pre-surgery 3D representation and the path determined from the real-time 2D images is minimized, using well known mathematical techniques, in a way that results in optimal registration of all three landmarks.

Embodiments described herein provide various benefits to applications requiring alignment of landmarks between 3D representations and 2D images. In particular, embodiments are directed towards fast and efficient methods of automatically aligning landmarks identified in pre-surgery 3D reconstructions to those landmarks as seen in 2D laparoscopic images captured during surgery. Embodiments require relatively simple camera position tracking technology, and image processing using well known mathematical transformations, to achieve accurate alignment of landmarks in the images viewed by the surgical team before and during surgery. Their actions during the surgical procedure are thus supported, without unnecessary distractions or complications related to image orientation interpretation or to operating additional imaging and tracking equipment.

Although the description has been presented with respect to particular embodiments thereof, these particular embodiments are merely illustrative, and not restrictive. For example, methods other than the Delaunay method may be used for the 3D reconstruction performed pre-surgery. 3D laparoscopy information may be derived from structure from motion or visual odometry. In some embodiments, additional point or line landmarks may be used.

Any suitable programming language can be used to implement the routines of particular embodiments including C, C++, Java, assembly language, etc. Different programming techniques can be employed such as procedural or object oriented. The routines can execute on a single processing device or multiple processors. Although the steps, operations, or computations may be presented in a specific order, this order may be changed in different particular embodiments. In some particular embodiments, multiple steps shown as sequential in this specification can be performed at the same time.

Particular embodiments may be implemented in a computer-readable storage medium for use by or in connection with the instruction execution system, apparatus, system, or device. Particular embodiments can be implemented in the form of control logic in software or hardware or a combination of both. The control logic, when executed by one or more processors, may be operable to perform that which is described in particular embodiments.

Particular embodiments may be implemented by using a programmed general purpose digital computer, by using application specific integrated circuits, programmable logic devices, field programmable gate arrays, optical, chemical, biological, quantum or nanoengineered systems, components and mechanisms may be used. In general, the functions of particular embodiments can be achieved by any means as is known in the art. Distributed, networked systems, components, and/or circuits can be used. Communication, or transfer, of data may be wired, wireless, or by any other means.

It will also be appreciated that one or more of the elements depicted in the drawings/figures can also be implemented in a more separated or integrated manner, or even removed or rendered as inoperable in certain cases, as is useful in accordance with a particular application. It is also within the spirit and scope to implement a program or code that can be stored in a machine-readable medium to permit a computer to perform any of the methods described above.

A "processor" includes any suitable hardware and/or software system, mechanism or component that processes data, signals or other information. A processor can include a system with a general-purpose central processing unit, multiple processing units, dedicated circuitry for achieving functionality, or other systems. Processing need not be limited to a geographic location, or have temporal limitations. For example, a processor can perform its functions in "real time," "offline," in a "batch mode," etc. Portions of processing can be performed at different times and at different locations, by different (or the same) processing systems. Examples of processing systems can include servers, clients, end user devices, routers, switches, networked storage, etc. A computer may be any processor in communication with a memory. The memory may be any suitable processor-readable storage medium, such as random-access memory (RAM), read-only memory (ROM), magnetic or optical disk, or other non-transitory media suitable for storing instructions for execution by the processor.

As used in the description herein and throughout the claims that follow, "a", "an", and "the" includes plural references unless the context clearly dictates otherwise. Also, as used in the description herein and throughout the claims that follow, the meaning of "in" includes "in" and "on" unless the context clearly dictates otherwise.

Thus, while particular embodiments have been described herein, latitudes of modification, various changes, and substitutions are intended in the foregoing disclosures, and it will be appreciated that in some instances some features of particular embodiments will be employed without a corresponding use of other features without departing from the scope and spirit as set forth. Therefore, many modifications may be made to adapt a particular situation or material to the essential scope and spirit.

We claim:

1. A method for automatic registration of landmarks in 3D and 2D images of an organ, the method comprising:
   using a first set of coordinates of identified first, second and third landmarks of the organ, derived from a 3D surface representation of the organ, and a second set of coordinates of the identified first, second and third landmarks of the organ, derived from first, second and third 2D laparoscopic images of the organ, to register the three landmarks as identified in the 3D surface representation with the three landmarks as identified in the first, second and third 2D images; the first and second sets of coordinates being expressed in a first frame of reference, corresponding to a first location and first orientation of a camera capturing the first 2D image;

wherein the third landmark comprises a plurality of points defining a path between two points characterizing the first and second landmarks;

wherein the identification of the first, second and third landmarks in the 3D representation and the 2D images is performed automatically;

wherein the derivation of the first and second sets of coordinates is performed automatically;

wherein the registration, based on the derived first and second sets of coordinates, is performed automatically;

wherein the first set of coordinates comprises:
- a first subset of location coordinates for the first landmark;
- a second subset of location coordinates for the second landmark; and
- a third subset of location coordinates comprising multiple location coordinates characterizing the third landmark;

wherein the second set of coordinates comprises:
- a fourth subset of location coordinates for the first landmark;
- a fifth subset of location coordinates for the second landmark; and
- a sixth subset of location coordinates comprising multiple location coordinates characterizing the third landmark;

wherein the fifth subset of location coordinates is derived by transforming a seventh subset of location coordinates of the second landmark expressed in a second frame of reference, corresponding to a second location and second orientation of a camera capturing the second and third 2D images.

2. The method of claim 1, wherein the camera that captures the first 2D image at the first location is the camera that captures the second 2D image at a second position in the vicinity of the second location after moving between the first location and the second location, and that captures the third 2D image at a third position, different from the second position, in the vicinity of the second location; and wherein analysis of the second and third 2D images, combined with analysis of tracking data, provided by tracking in 3D the motion of the camera between the first location and first orientation and the second location and second orientation, allows a spatial 3D relationship between the first location and first orientation and the second location and second orientation to be determined, providing transform data required to accomplish the transformation of the seventh subset to the fifth subset.

3. The method of claim 1, wherein the camera that captures the first 2D image at the first location is a first camera, which is then moved to the second location;

wherein the camera that captures the second and third 2D images, capturing the second 2D image at a second position in the vicinity of the second location, and capturing the third 2D image at a third position, different from the second position, in the vicinity of the second location is a second camera; and wherein analysis of the second and third 2D images combined with analysis of tracking data, provided by tracking in 3D the motion of the first camera between the first location and first orientation and the second location and second orientation, allows the spatial 3D relationship between the first location and first orientation and the second location and second orientation to be determined, providing transform data required to accomplish the transformation of the seventh subset to the fifth subset.

4. The method of claim 1, wherein the 3D surface representation of the organ is computationally reconstructed from a plurality of CT scans of the organ.

5. The method of claim 4, wherein the reconstruction comprises using a Delaunay method of image processing.

6. The method of claim 4, wherein the reconstruction of the 3D surface representation is performed in advance of surgery, and wherein the 2D images are captured during surgery using a laparoscopic camera system.

7. The method of claim 1, wherein using the first and second sets of coordinates to register the three landmarks comprises:

using an estimate of position and orientation of a camera capturing one of the 2D images to project the first set of coordinates from 3D space to the image plane of the 2D image; and minimizing the error between the projection of the third subset of location coordinates, and the sixth subset of location coordinates characterizing the third landmark, while aligning the projection of the first and second subsets of location coordinates to the fourth and fifth subsets of location coordinates respectively, within predetermined limits.

8. The method of claim 1, wherein the organ is a liver.

9. An apparatus comprising:

one or more processors; and logic encoded in one or more non-transitory media for execution by the one or more processors and when executed operable to automatically register landmarks in 3D and 2D images of an organ, wherein the automatic registration comprises:

using a first set of coordinates of identified first, second and third landmarks of the organ, derived from a 3D surface representation of the organ, and a second set of coordinates of the identified first, second and third landmarks of the organ, derived from first, second and third 2D laparoscopic images of the organ, to register the three landmarks as identified in the 3D surface representation with the three landmarks as identified in the first, second and third 2D images; the first and second sets of coordinates being expressed in a first frame of reference, corresponding to a first location and first orientation of a camera capturing the first 2D image;

wherein the third landmark comprises a plurality of points defining a path between two points characterizing the first and second landmarks;

wherein the identification of the first, second and third landmarks in the 3D representation and the 2D images is performed automatically;

wherein the derivation of the first and second sets of coordinates is performed automatically;

wherein the registration, based on the derived first and second sets of coordinates, is performed automatically;

wherein the first set of coordinates comprises:
- a first subset of location coordinates for the first landmark;
- a second subset of location coordinates for the second landmark; and a third subset of location coordinates comprising multiple location coordinates characterizing the third landmark;

wherein the second set of coordinates comprises:
  a fourth subset of location coordinates for the first landmark;
  a fifth subset of location coordinates for the second landmark; and
  a sixth subset of location coordinates comprising multiple location coordinates characterizing the third landmark;

wherein the fifth subset of location coordinates is derived by transforming a seventh subset of location coordinates of the second landmark expressed in a second frame of reference, corresponding to a second location and second orientation of a camera capturing the second and third 2D images.

10. The apparatus of claim 9,
wherein the camera capturing the first 2D image at the first location also captures the second 2D image at a second position in the vicinity of the second location, and captures the third 2D image at a third position, different from the second position, in the vicinity of the second location; and
wherein data required to accomplish the transformation of the seventh subset to the fifth subset is determined by tracking in 3D the motion of the camera between the first location and first orientation and the second location and second orientation.

11. The method of claim 9,
wherein the camera capturing the first 2D image is a first camera;
wherein a second camera captures the second and third 2D images, capturing the second 2D image at a second position in the vicinity of the second location, and capturing the third 2D image at a third position, different from the second position, in the vicinity of the second location; and
wherein analysis of the stereo pair of second and third 2D images allows a spatial 3D relationship between the first location and first orientation and the second location and second orientation to be determined, providing data required to accomplish the transformation of the seventh subset to the fifth subset.

12. An apparatus comprising:
one or more processors; and
software encoded in one or more non-transitory computer-readable media for execution by the one or more processors and when executed operable to automatically register landmarks in 3D and 2D images of an organ, the automatic registration comprising:
using a first set of coordinates of identified first, second and third landmarks of the organ, derived from a 3D surface representation of the organ, and a second set of coordinates of the identified first, second and third landmarks of the organ, derived from first, second and third 2D laparoscopic images of the organ, to register the three landmarks as identified in the 3D surface representation with the three landmarks as identified in the first, second and third 2D images; the first and second sets of coordinates being expressed in a first frame of reference, corresponding to a first location and first orientation of a camera capturing the first 2D image;

wherein the third landmark comprises a plurality of points defining a path between two points characterizing the first and second landmarks;
wherein the identification of the first, second and third landmarks in the 3D representation and the 2D images is performed automatically;
wherein the derivation of the first and second sets of coordinates is performed automatically;
wherein the registration, based on the derived first and second sets of coordinates, is performed automatically;
wherein the first set of coordinates comprises:
  a first subset of location coordinates for the first landmark;
  a second subset of location coordinates for the second landmark; and
  a third subset of location coordinates comprising multiple location coordinates characterizing the third landmark;
wherein the second set of coordinates comprises:
  a fourth subset of location coordinates for the first landmark;
  a fifth subset of location coordinates for the second landmark; and
  a sixth subset of location coordinates comprising multiple location coordinates characterizing the third landmark;
wherein the fifth subset of location coordinates is derived by transforming a seventh subset of location coordinates of the second landmark expressed in a second frame of reference, corresponding to a second location and second orientation of a camera capturing the second and third 2D images.

13. The apparatus of claim 12,
wherein the camera capturing the first 2D image at the first location also captures the second 2D image at a second position in the vicinity of the second location, and captures the third 2D image at a third position, different from the second position, in the vicinity of the second location; and
wherein data required to accomplish the transformation of the seventh subset to the fifth subset is determined by tracking in 3D the motion of the camera between the first location and first orientation and the second location and second orientation.

14. The method of claim 12,
wherein the camera that captures the first 2D image at the first location and is then moved to the second location is a first camera;
wherein the camera that captures the second and third 2D images, capturing the second 2D image at a second position in the vicinity of the second location, and capturing the third 2D image at a third position, different from the second position, in the vicinity of the second location is a second camera; and
wherein analysis of the second and third 2D images combined with analysis of tracking data, provided by tracking in 3D the motion of the first camera between the first location and first orientation and the second location and second orientation, allows a spatial 3D relationship between the first location and first orientation and the second location and second orientation to be determined, providing transform data required to accomplish the transformation of the seventh subset to the fifth subset.

* * * * *